US00PP15767P2

(12) United States Plant Patent
Cosner et al.

(10) Patent No.: US PP15,767 P2
(45) Date of Patent: May 17, 2005

(54) ***IMPATIENS* PLANT NAMED 'TICOPINK'**

(50) Latin Name: *Impatiens walleriana*
Varietal Denomination: TiCoPink

(76) Inventors: Harlan B. Cosner, 14389 E. Evans Creek Rd., Rogue River, OR (US) 97537; Susan Cosner, 14389 E. Evans Creek Rd., Rogue River, OR (US) 97537

( * ) Notice: Subject to any disclaimer, the term of this patent is extended or adjusted under 35 U.S.C. 154(b) by 12 days.

(21) Appl. No.: 10/783,329

(22) Filed: Feb. 20, 2004

(51) Int. Cl.[7] ..... A01H 5/00
(52) U.S. Cl. ..... Plt./317
(58) Field of Search ..... Plt./317

*Primary Examiner*—Kent Bell
(74) *Attorney, Agent, or Firm*—Ganz Law, PC; Bradley M. Ganz

(57) ABSTRACT

A new, double *Impatiens walleriana* plant named 'TiCoPink'; producing pink flowers; dark green foliage; compact growth habit; fully double flowers held above or beyond the foliage on strong peduncles and pedicels; and a compact mounded growth habit.

1 Drawing Sheet

Latin name of the genus and species and variety denomination: *Impatiens walleriana* plant and known by the cultivar name 'TiCoPink'.

BACKGROUND OF THE INVENTION

Field of Invention

The present invention comprises a new and distinct cultivar of plant, botanically known as *Impatiens walleriana,* and hereinafter referred to by the cultivar name of 'TiCoPink'.

1. The plants are useful in landscaping, window and hanging baskets and flower gardens.
2. The plant is an *Impatiens walleriana.*
3. The plants are generally classed as an annual bedding plant.

Description of the Relevant Prior Art

1. The pollen parent is an unpatented pollen producing double *Impatiens walleriana* coded P-M-BR-3, and the seed parent is an unpatented semi-double *Impatiens* coded P-BR-318. 'TiCoPink' is both male and female sterile. Cultivar is both female and male sterile. Both parents are capable of both seed and pollen production.
2. The seed parent was a Pink flowered cultivar and the pollen parent was a Scarlet flowered cultivar, neither parent is either patented or commercially available. The cross was made in the breeders controlled breeding program at Rogue River, Oreg. The first asexual reproduction was also made at Rogue River, Oreg. by lateral stems with two or more leaves. Successive asexual generations produced from cuttings with two or more leaves have shown the cultivar to be stable and reproduced true to type.

COMPARISON

1. The plant is compared to 'TiLip', U.S. Plant Pat. No. 12,855.
2. The flower color of 'TiCoPink' is darker than that of 'TiLip'.
3. See comparison chart labeled Chart 1.

SUMMARY OF THE INVENTION

The cultivar is unique either in one or a combination of the characteristics described herein. It is a new, double *Impatiens walleriana* producing pink flowers; dark green foliage; compact growth habit; fully double flowers held above or beyond the foliage on strong peduncles and pedicels; a compact mounded growth habit.

DESCRIPTION OF THE PHOTOGRAPHS

The attached color photographs illustrate a plant of 'TiCoPink' grown in winter and just beginning to mature. Variations between the written description and the colors in the photographs may occur due to the type of film and/or light reflectance and the type of light captured by the film. In the event there are such variations, the written description shall control.

PLANT DESCRIPTION

The following description was taken at Rogue River, Oreg. on Feb. 7, 2004. The description is of a plant of 'TiCoPink' similar to the one shown in the photograph.

The following description was taken from a plant approximately 12-weeks of age under the following environment and cultural practices at Rogue River, Oreg. Phenotypical variations may result in plants grown under conditions and locations other than those listed herein.

Container: 6 inch *Azalea* pot.
Medium: Peat-lite type of soilless medium.
Greenhouse covering: Double layer Polyethelene with 50% shade applied above the covering.
Minimum temperature: 65° F.
Maximum temperature: 75° F.
Light levels: 1000 to 1500 ft candles.
Fertilizer: 20-10-20 with trace elements applied twice followed by one leaching with clear water.
Cutting type: Lateral stems with two or more leaves.
Propagation:
*Type of cutting.*—Lateral stems with two or more leaves.

*Time to initiate roots.*—Generally about 7 to 10 days at soil temperature of 72° F.

Appearance and form of mature plant:

*Note.*—All size measurements for plant, stems, foliage, flowers, peduncles, pedicels, buds, and sepals are taken during winter, low light conditions when the above are the smallest. Spring and summer high light sizes are generally much larger than the sizes that are described below.

*Growth habit.*—Mounded and of compact-medium vigor.

*Plant size.*—Plants mature at about 16 cm in height and about 30 cm in width. Both of these measurements are a function of age, environmental and cultural practices, and can vary accordingly.

*Rooting habit.*—The roots are fibrous and well branched.

*Rooting ability.*—Easy, no hormones needed.

*Stems.*—Stems are freely produced, and no pinching to induce branching is needed. Color is translucent and lighter than 145D with stippling of very small markings that are difficult to determine but which appear to be close to 187C. The stems at maturity are generally at least 3 mm in diameter at the internodes, and the internode length is generally at least 0.5 cm in length.

*Foliage.*—Shape is ovate with cuneate to attenuate base; crenate margin, margin having tiny spines of an undeterminable reddish to brownish red color and each being less than 1 mm in length and protruding outwards in a perpendicular direction from leaf edge and parallel to the flat surfaces of the leaf, between the lobes of the crenate margin; and an acuminate apex. Size of largest is about 3 cm long; about 2.75 cm wide.

*Foliage color.*—Adaxial surface close to 147A; abaxial surface close to 147C with dark markings close to a greenish tinged 178A; abaxial surface venation is close to 148A; adaxial surface venation, main vein at base is closest to 146A, lateral veins are close to 146A.

*Foliage texture.*—Smooth and flat.

*Petioles.*—Longest petioles are about 3 cm long, half round, flat to slightly convex on upper surface which is about 2 mm wide, depth of about 1.5 mm. Adaxial surface color appears to be 146B stippled with tiny reddish markings that are difficult to determine but appear to be close to 178A to 178B; abaxial surface color appears to be close to 146C to 146D with stippling of very tiny marks of what appear to be 178A to 178B.

*Flower habit.*—Flowers are produced continuously throughout the flowering season.

*Natural flowering season.*—All year around in greenhouse conditions, and the frost-free period from spring through fall when planted outdoors.

*Duration of flower.*—Each flower generally lasts about 5 days at 75° F. maximum and 70° F. minimum temperature.

*Flowers borne.*—Above or beyond the foliage.

*Flower texture.*—Smooth and satiny.

*Flower color.*—Petals/petaloids — Adaxial surface is close to 55B with a basal spot that appears close to 67A. Abaxial surface is closest to 55B at the margins and changes gradually to 55C toward the base with a basal spot of close to 55A.

*Quantity.*—Usually two or more open flowers per stem and generally 15 or more from visible buds to fully mature flowers.

*Petal/petaloid count.*—Generally 25 or more.

*Size.*—Flowers are generally at least 3.5 cm in diameter; generally at least 1 cm deep with largest petals/petaloids. The largest petals/petaloids are generally at least 1.5 cm wide and at least 1.5 cm long; obovate to exaggerated obovate in shape with obtuse to retuse apex, entire margin, and cuneate to obtuse base. The above measurements refer to the average flowers.

*Flower buds.*—The buds prior to opening are about 1 cm in length; about 0.75 cm. in diameter; shape is ovate. Bud color prior to opening is close to 145A on top and close to 149D on bottom.

*Peduncles.*—Generally at least 1 cm long; about 2 mm in diameter; colored close to 146D. Good strength.

*Pedicels.*—Generally two or more per peduncle. Each is generally at least 1.75 cm in length, and at least 1.5 mm in diameter. Color is close to 146D. Good strength.

*Calyx.*—Calyx consists of generally one sepal and one spur. The spur is generally at least 1.75 cm long, and about 2 mm in diameter at sepal end; shape is an acicular tapering tube about 1 mm in diameter at the apex, and it is attached toward the base of the sepal in a peltate manner. Color is close to 178A at apex, is an orangish-green that neither matches, nor is very close to any color in the chart, with the closest color in the chart being 166D at base. The sepal generally measures at least 0.75 cm wide, and at least 1.1 cm long; ovate in shape with an acute apex, entire margin, and obtuse to cordate base; abaxial surface is lighter than 145D, with a base spot of close to 74B where the spur connects; the adaxial surface is close to 145D and has a basal spot that appears close to 70A where the spur attaches.

*Reproductive organs.*—The reproductive organs are replaced with sterile petaloids.

*Disease resistance.*—Disease resistance has not been tested.

*Dampness resistance.*—The plant has shown a good ability to hold the flowers in an outward manner during summer rains.

*Heat tolerance.*—The plant has shown a good tolerance to temperatures exceeding 100° F. at Rogue River by flowering continuously during temperatures as high as 113° F.

CHART 1

COMPARISON CHART TO PRIOR ART

| | 'TiCoPink' | 'TiLip' |
|---|---|---|
| Stems - color | Color is lighter than 145D with tiny markings close to 187C. | Close to 146B with 178B markings. |
| Foliage - Size | About 3 cm long; about 2.75 cm wide. | About 5 cm long, about 4.5 cm wide. |
| Abaxial - color | Close to 147C with markings of a greenish tinged 178A. | 146B. |
| Foliage - Abaxial venation color | Close to 148A. | 146A. |
| Foliage - Adaxial color | Close to 147A. | Darker than 146A. |
| Foliage - Adaxial | Main vein at base is | 146A. |

CHART 1-continued

COMPARISON CHART TO PRIOR ART

| | 'TiCoPink' | 'TiLip' |
|---|---|---|
| venation color | closest to 145A, lateral veins appear closest to 146A. | |
| Petiole - Size | About 3 cm long, 2 mm wide, depth of about 1.5 mm. | About 2 cm long and about 3 mm diameter 1.5 mm in depth. |
| Adaxial color | Appears to be 146B; with stippling of 178A to 178B. | 146C with stippling close to 178A. |
| Petiole Abaxial color | Appears close of 146C to 146D with stippling of 178A to 178B. | 146D. |
| Petal/Petaloid - Size | Generally at least 1.5 cm. wide and at least 1.5 cm. long. | About 2.3 cm in length, about 1.8 cm in width. |
| Abaxial color | Deep close to 55B changing to 55C with a basal spot close to 55A. | 65C, with basal spot close to 67B. |
| Petal/Petaloid Adaxial color | Close to 55B with a basal spot close to 67A. | 62B to 62C with darker veining close to 62A. |
| Peduncle - Size | About 1 cm long; about 2 mm in diameter. | About 2 cm long, about 2 mm in diameter. |
| Color | Close to 146D. | 146B with stippling close to 178B |
| Pedicel- Size | Generally at least 1.75 cm in length, and at least 1.5 mm in diameter. | About 1.8 cm in length, about 1 mm diameter. |
| Color | Close to 146D. | 146C with stippling close to 178A. |
| Sepal - Size | Generally measures about 0.75 cm wide and about 1.1 cm long. | About 0.8 cm wide and about 1.2 cm long. |
| Adaxial color | Close to 145D with a spot around where the spur connects close to 70A. | 142D with basal spot close to 66C. |
| Sepal Abaxial color | Lighter than 145D with a spot where the spur attaches close to 74B. | 142C. |
| Spur - Size | Generally at least 1.75 cm long, and about 2 mm in diameter at sepal end; and about 1 mm at apex. | About 3 cm long |

CHART 1-continued

COMPARISON CHART TO PRIOR ART

| | 'TiCoPink' | 'TiLip' |
|---|---|---|
| Color | Color is close to 178A at apex, is an orangish-green that neither matches, nor is very close to any color in the chart with the closest color in the chart being 166D at base. | Color at apex 177C and 194B at base with markings of 178B. |
| Buds - Size | About 1 cm in length; about 0.75 cm in diameter; | About 1.2 cm long, about 0.8 cm diameter. |
| Color | Bud color is close to 145A on top and close to 149D on bottom. | 145A top, 145B. |

COLOR CODE CHART

| | |
|---|---|
| Stems: | 145D, 187C |
| Foliage Abaxial surface: | 147C, 178A |
| Foliage Abaxial surface venation: | 148A |
| Foliage Adaxial surface: | 147A |
| Foliage Adaxial surface venation: | 146A |
| Petiole Abaxial surface: | 146C, 146D, 178A, 178B |
| Petiole Adaxial surface: | 146C, 146D, 178A, 178B |
| Petals/Petaloids Abaxial: | 55B, 55C, 55A |
| Petals/Petaloids Adaxial surface: | 55B, 67A |
| Buds: | 145A, 149D |
| Peduncles: | 146A |
| Pedicels: | 146A |
| Sepals adaxial surface: | 145D, 70A |
| Sepals abaxial surface: | 145D, 74B |
| Spur: | 178A, 166D |

It is claimed:

1. A new and distinct cultivar of double *Impatiens walleriana* plant named 'TiCoPink', as illustrated and described.

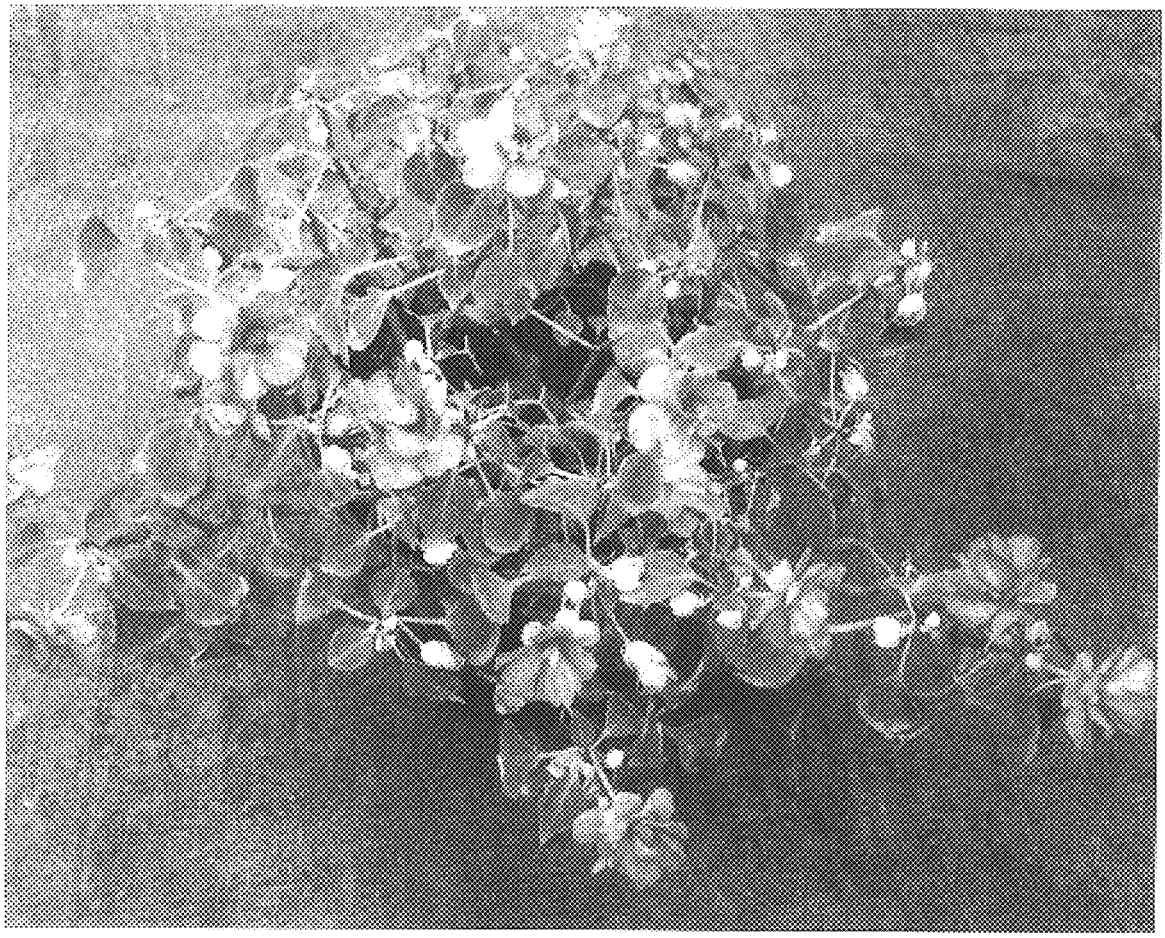

* * * * *